United States Patent
Mihura et al.

(10) Patent No.: US 11,197,443 B2
(45) Date of Patent: Dec. 14, 2021

(54) METHODS FOR IMPROVING SEED PRODUCTION IN MAIZE

(71) Applicant: Pioneer Hi-Bred International, Inc., Johnston, IA (US)

(72) Inventors: Eduardo J Mihura, Urbandale, IA (US); Scott M Nelson, Urbandale, IA (US); Imad Saab, Urbandale, IA (US); Adda C Sayers, Urbandale, IA (US); Aaron J Schwarte, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 982 days.

(21) Appl. No.: 13/649,435

(22) Filed: Oct. 11, 2012

(65) Prior Publication Data

US 2013/0096004 A1 Apr. 18, 2013

Related U.S. Application Data (60) Provisional application No. 61/547,142, filed on Oct. 14, 2011.

(51) Int. Cl.
*A01H 5/10* (2018.01)
*A01H 6/46* (2018.01)

(52) U.S. Cl.
CPC ............ *A01H 6/4684* (2018.05); *A01H 5/10* (2013.01); *Y02A 40/10* (2018.01)

(58) Field of Classification Search
None
See application file for complete search history.

(56) References Cited

U.S. PATENT DOCUMENTS

| | | | |
|---|---|---|---|
| 4,069,614 A * | 1/1978 | Hicks et al. ............. | A01G 7/00 47/58.1 R |
| 5,491,125 A | 2/1996 | Albrecht et al. | |
| 5,518,989 A * | 5/1996 | Martin et al. ............ | A01C 1/00 504/116.1 |
| 6,162,974 A | 12/2000 | Martin et al. | |
| 2011/0036002 A1 | 2/2011 | Alston et al. | |

FOREIGN PATENT DOCUMENTS

| | | |
|---|---|---|
| WO | 199520312 A1 | 8/1995 |
| WO | 1995020312 A1 | 8/1995 |

OTHER PUBLICATIONS

Declaration of Stanley Bernard (2014).*
Romeis et al., Nature Biotech. 24(1):63-71 (2006).*
Baudet, Ph.D. Dissertation (1988).*
Hunter, Ph.D. Dissertation (1989).*
Afuakwa, JJU, Ph.D. Thesis, Univ. of Minn. (1982).*
Afukawa JJ, Ph.D. Thesis, Univ. of Minn. (1982).*
Defol Product Literature (2011).*
Romeis et al., Nat Biotech 24(1):63-71 (2006).*
Knittle & Burris, Crop Sci. 16:851-55 (1976).*
Hunter et al. (1991) Crop Sci 31:1309-13.*
Ma & Dwyer (2001) Can J Plant Sci 81:225-32.*
Ciampitti et al., Corn Growth and Development, https://www.bookstore.ksre.ksu.edu/pubs/MF3305.pdf, Jun. 2016.*
Hallauer et al. (1988) "Corn Breeding," Iowa St. Univ. Digital Repository.*
Wright, H. (1980) "Commercial Hybrid Seed Production" in: W.R. Fehr, H.H. Hadley, eds., Hybridization of Crop Plants, ASA, CSSA, Madison, WI, pp. 161-176.*
Afuakwa, JJ, Ph.D. Thesis, Univ. of Minn. (1982).*
Rajni, et al.; "Effect of Chemical Defoliation on Boll Opening Percentage, Yield and Quality Parameters of Bt Cotton (*Gossypium hirsutum*)"; Indian Journal of Agronomy (Mar. 2011) 56(1):74-77.
Barimavandi, et al.; "Effect of Different Defoliation Treatments on Yield and Yield Components in maize (*Zea mays* L.) Cultivar of S.C704"; Australian Journal of Crop Science (2010) 4(1):9-15.
Umashankara; "Influence of Stages and Levels of Defoliation on Seed Yield and Quality of Fodder Maize (cv. South African Tall)" Masters Thesis University of Agricultural Sciences, Dharwad.
Casselman, T.W. et al., Corn Topping Prior to Harvest, Agricultural Engineering Oct. 1961, 541-545 (1961) ("Casselman").
Cooper, G.S., Preharvest Chemical Top-Killing as a Possible Aid in the Natural Drying and Harvesting of Small Grains, Corn and Soybeans, Ph.D Thesis, Univ. of Ill. (1953) ("Cooper").
Cornelius, P.L., Effect of Topping on Moisture Loss, Dry Matter Accumulation and Yield of Corn Grain, M.S. Thesis, Iowa State Univ. (1959) ("Cornelius 1959").
Cornelius, P.L. et al., Effect of Topping on Moisture Loss, Dry Matter Accumulation, and Yield of Corn Grain, Agronomy J. 53:285-289 (1961) ("Cornelius 1961").
Dungan, G., Losses to the Corn Crop Caused by Leaf Injury, (1934) ("Dungan 1934").
Dungan et al., Corn Grows Some Even After Hail Destroys All Blades, (1936) ("Dungan 1936").
Egharevba, P.N., Dry Matter Accumulation in Maize: The Effects of Differential Defoliation Applied at Various Stages of Plant Development, Dissertation, Univ. of Missouri—Columbia (1973) ("Egharevba 1973").
Egharevba, P.N. et al., Dry Matter Accumulation in Maize in Response to Defoliation (1976) ("Egharevba 1976").
Eldredge, J.C., The Effect of Injury in Imitation of Hail Damage on the Development of Corn, Thesis, Iowa St. College (1933) ("Eldredge 1933").
Eldredge, J.C. et al., The Effect of Injury in Imitation of Hail Damage on the Development of the Corn Plant, Iowa Agric. Hom Econ. Exp. Stn. Res. Bull. 185 (1935) ("Eldredge 1935").
Eldredge, J.C., Hail Damage to Corn. Iowa Agr. Exp. Sta. Bul. 348 (1936) ("Eldredge 1936").

(Continued)

*Primary Examiner* — Russell T Boggs (57) ABSTRACT

Defoliation of maize plants, based on percent seed moisture, has advantageous outcomes including greater number of seeds per pound; increased volume or proportion of saleable seed per field and per female acre; decreased discard of seed due to commercially undesirable size or shape; lower moisture content of seed at harvest; earlier harvest date; less fuel and time expended in drying seed for storage; improved performance in laboratory tests for germination at cold temperatures; improved seed treatment efficacy; improved emergence under stress in field conditions; improved plantability in mechanical systems; more uniform stand; fewer runt plants and improved grain yield.

29 Claims, 8 Drawing Sheets

(56) References Cited

OTHER PUBLICATIONS

Hicks et al., Defoliation Effects on Corn Hybrids Adapted to the Northern Corn Belt (1977) ("Hicks 1977").
Hicks, D.R. & Crookston, R.K., Early Growth Alteration to Increase Corn Grain Meld, U.S. Pat. No. 4,069,614 ("Hicks '614").
Vasilas, B.L. & Seif, R.D., Effect of Defoliating Corn Inbreds on Seed Quality, J. Seed Tech., 121-128 (1986) ("Vasilas 1986").
Hunter, J.L. et al., The Influence of Seed Maturity Upon Seed Viability and Vigor in Corn (Zea mays L.), Agron. Abstracts (1987) ("Hunter 1987").
Hunter, J.L. & Tekrony, D.M., Seed Maturation and Vigor in Corn (Zea mays L.) as Influenced by Defoliation, Agron. Abstracts (1988) ("Hunter 1988a").
Hunter, J.L., The Relationship of Corn Seed Maturity with Seed Vigor and Assimilate Uptake, Seminar (Oct. 1988) ("Hunter 1988b").
Hunter, J.L., Relationship Between the Stage of Corn Seed Maturation and Assimilate Supply, Assimilate Uptake, and Seed Quality, Dissertation, Univ. of Ky. (1989) ("Hunter 1989") 11-160.
Hunter, J.L. et al., Corn Seed Maturity Indicators and Their Relationship to Uptake of Carbon-14 Assimilate, Crop Science, 31:1309-1313 (1991) ("Hunter 1991").
Jones, J.B. et al., Effect of Date of Topping Upon Corn Yields in Ohio, Crop Science 1:303 (1961) ("Jones").
Kaerwer, H.E., Maturity in Relation to Seedling Vigor, Am. Seed Trade Assoc., Pub. 8 (Dec. 1953) ("Kaerwer").
Kiesselback & Lyness, Simulated Hail Injury of Corn, Univ. of Neb. Agricultural Experiment Station Bulletin 377, Jun. 1945 ("Kiesselback").
Knittle, K.H. & Burris, J.S., Effect of Kernel Maturation on Subsequent Seedling Vigor in Maize, Crop Science Society of America, 16:851-855 (Nov.-Dec. 1976) ("Knittle").
Major, D.J., Effect of Simulated Frost Injury Induced by Paraquat on Kernel Growth and Development in Corn, Can J. Plant Sci. 60:419-426 (1979) ("Major").
Martin, B. et al., Seed Vigor by Pre-Harvest Defoliation of Maize Plants, U.S. Pat. No. 5,518,989, cols. 1:15-2:23, and U.S. Pat. No. 6,162,974, cols. 1:19-2:27 ("Martin background") Date of Patent Dec. 19, 2000.
Phillips, C.A. & Archer, H.W., Desiccant and Defoliating Spray Composition for Leguminous Plants, U.S. Pat. No. 4,192,668 ("Phillips") Date of Patent Mar. 11, 1980.
Raymundo, Epidemiology of Northern Corn Leaf Blight as Affected By Host Resistance and Yield Losses Following Simulated Epidemics, Ph.D. Thesis, Univ. of Illinois (1978) ("Raymundo").
Reiss, F., Relation of Moisture Content and Drying Temperature to the Viability and Seedling Vigor of Maize, Germinated by Different Methods, Thesis, Iowa State College (1944) ("Reiss").
Rush, G.E. & Neal, N.P., The Effect of Maturity and Other Factors on Stands of Corn at Low Temperatures, Am. Society of Agronomy, vol. 43:112-116 (Mar. 1951) ("Rush").
Russell, Effect of Defoliation Treatments at Various Stages of Plant Development and Row Spacings on Corn (Zea mays L.) Production, Ohio St. Univ. (1967) ("Russell").
Tollenaar, et al., Effect of Defoliation on Kernel Development in Maize, Can. J. Plant Sci. 58: 207-212 (1978) ("Tollenaar 1978").
Weather History for Urbana, Illinois Retrieved from http://www.almanac.com/weather/history/IL/Urbana/1983-07-24 on Jan. 14, 2013.
Siray, "Effects of Partial Defoliation of Corn Plant by Topping on the Yield of Corn Grain and its Quality and Nutritional Efficiency of Tops" (1976), 1-9.
Petition for inter partes review of U.S. Pat. No. 6,162,974 in IPR 2013-00023 Oct. 17, 2012.
'974 Exhibit List (inter partes review of U.S. Pat. No. 6,162,974) in IPR 2013-00023 Oct. 17, 2012.
Burris Declaration dated Oct. 16, 2012 (inter review of U.S. Pat. No. 6,162,974) in IPR 2013-00023 Oct. 17, 2012.
Patent Owner Preliminary Response Inter Partes Review of U.S. Pat. No. 5,518,989 in IPR2013-00022 Jan. 17, 2013.
Patent Owner Exhibit List (inter partes review of U.S. Pat. No. 6,162,974) in IPR 2013-00023 Jan. 17, 2013.
Patent Owner Preliminary Response (inter partes review of U.S. Pat. No. 6,162,974) in IPR 2013-00023 Jan. 17, 2013.
Patent Owner Exhibit for Inter Partes Review of U.S. Pat. No. 5,518,989 in IPR2013-00022 Jan. 17, 2013.
Decision-Denying Inter Partes Review for IPR 2013-00023 (inter partes review of U.S. Pat. No. 6,162,974) Apr. 11, 2013.
Allen, R.R. et al., Topping Corn and Delaying Harvest for Field Drying, 1982 Transactions of the A.S.A.E. 1529-1532 (1982) ("Allen").
Hunter, et al Abstract: 80th American Society of Agronomy Annual Meetings New Initiatives in Shaping our Future; Nov. 27-Dec. 2, 1988; Anaheim, CA.
Vasilas, et al, "Effect of Defoliating Corn Inbreds on Seed Quality" Journal of Seed Technology, 121-128 (1986).
Vasilas, et al, "Defoliation Effects on Two Corn Inbreds and their Single-Cross Hybrid" Agronomy Journal, vol. 77(5) 816-820 (1985).
Alcantara, et al, "Glyphosate as Harvest Aid for Corn (Zea mays)" Weed Technology: A Journal of the Weed Science Society of America, vol. 2(4) 410-413 (1988).
Major, "Effect of Simulated Frost Injury Induced by Paraquat on Kernel Growth and Development in Corn" Can. J. Plant Sci 60:419-416(1980).
File History U.S. Pat. No. 5,518,989 Oct. 11, 2012.
File History U.S. Pat. No. 6,162,974 Oct. 11, 2012.
Calderbank et al., Diquat and Paraquat., Herbicides: Chemistry, Degradation, and Mode of Action, vol. 2, 2d Edition (Kearney et al., eds.) pp. 529-532 (2001).
Neild, et al, "Growing Degree Days" Neb Guide, G1-G2 (1975).
Calderbank, et al, "Diquat and Paraquat" ICI Plant Protection Division Jealott's Hill Research Station, 501-540 (1976).
Pages of Dissertation, Sciences and Engineering vol. 50(8) (1990).
Burris Declaration Part 1 dated Oct. 16, 2012 in IPR 2013-00023 (inter partes review of U.S. Pat. No. 6,162,974) Oct. 17, 2012.
Burris Declaration Part 2 dated Oct. 16, 2012 in IPR 2013-00023 (inter partes review of U.S. Pat. No. 6,162,974) Oct. 17, 2012.
Burris CV dated Oct. 16, 2012 in IPR 2013-00023 (inter partes review of U.S. Pat. No. 6,162,974), in IPR 2013-00022 (inter partes review of U.S. Pat. No. 5,518,989) May 21, 1996.
Barger, "Weekly Weather and Crop Bulletin" US Department of Commerce vol. 56:18 1-12 (1969).
Eckert, et al, "Maturity Rating Systems for Corn" National Corn Handbook 1-3 (1986).
Burris, et al, "Drying High-Moisture Seed Corn" Proceedings of the Thirty-Fifth Annual Corn & Sorghum Industry Research Conference 116-132 (1980).
Monsanto Company's 974 Exhibit List Inter Partes Review of IPR 2013-00023 U.S. Pat. No. 6,162,974, Oct. 17, 2012.
Tekrony, et al, "Effect of Seed Maturation and Genotype on Seed Vigor in Maize" Crop Science, vol. 35(3) 857-862 (1995).
Weather History for Urbana, Illinois Retrieved from http://www.almanac.com/weather/history/IL/Urbana/1983-07-04 on Jan. 14, 2013.
Record of Climatological Observations for Urbana, IL US, US Department of Commerce National Climatic Data Center Dec. 18, 2012.
GDD Accumulation in Urbana IL The Old Farmer's Almanac (www.alamanac.com) 1983.
Camery et al., Effects of Certain Components of Simulated Hail Injury on Soybeans and Corn, Iowa Agric. and Home Econ. Exp. Stn. Res. Bull. 400 (Oct. 1953) ("Camery").
Plaintiff Pioneer Hi-Bred International, Inc's Answer and Affirmative Defenses to Monsanto Company's Amended Counter Claims filed Oct. 26, 2012 in the United States District Court for Southern District of Iowa Central Division.
Petition for Inter Partes Review of U.S. Pat. No. 5,518,989 in IPR 2013-00022 Oct. 17, 2012.
'989 Exhibit List for inter partes review of U.S. Pat. No. 5,518,989 in IPR 2013-00022 Oct. 17, 2012.
Decision—Denying Inter Partes Review for IPR 2013-00022 (inter partes review of U.S. Pat. No. 5,518,989) Apr. 11, 2013.
Exhibit List for IPR 2013-00022 (inter partes review of U.S. Pat. No. 5,518,989) Feb. 5, 2013.

(56) References Cited

OTHER PUBLICATIONS

Monsanto Answer, Affirmative, Defenses and Counterclaim Dec. 9, 2011.
Monsanto Corrected Brief in support of Motion for Judgment on the pleadings Sep. 24, 2012.
Pioneer Brief in Opposition to Monsanto's Motion for Judgment on the pleadings Oct. 29, 2012.
Monsanto Reply in support of it's Motion for Judgment on the pleadings Nov. 8, 2012.
Monsanto Supplemental Initial Invalidity Contentions with Exhibit A Nov. 30, 2012.
Afuakwa, J. J., A Re-evaluation of Some Aspects of the Growth and Maturation of the Corn (*Zea Mays*, L), Ph D Thesis, Univ. of Minn. (1982) ("Afuakwa 1982").
Afuakwa, J.J. et al., Effect of Temperature and Sucrose Availability on Kernel Black Layer Development in Maize, Crop Sci. Soc. Am. 24(2):285-288 (Mar.-Apr. 1984) ("Afuakwa 1984a").
Afuakwa, J.J. & Crookston, R.K., Using the Kernel Milk Line to Visually Monitor Grain Maturity in Maize, Crop Sci. Soc. Am. 24(4):687-691 (Jul.-Aug. 1984) ("Afuakwa 1984b").
Hooker, A.L., Estimating Disease Losses Based on the Amount of Healthy Leaf Tissue During Plant Reproductive Period, Genetika, vol. 11(2), 181-192. 1979. (Hooker).
Office Action from the Eurasian Patent Office for Application Serial #201490784 Office Action Received Nov. 4, 2015. Original and translated version submitted.
Communication from the European Patent Office dated Aug. 26, 2015 for Application No. 12 778 014.6.
International Preliminary Report on Patentability Chapter I dated Apr. 15, 2014 for PCT application No. PCT/US2012/059747.
Written Opinion of the International Search Authority dated Apr. 14, 2014 for PCT application No. PCT/US2012/059747.
International Search Report dated Feb. 1, 2013 for PCT application No. PCT/US2012/059747.
Wark E. Westgate, Jon Lizaso, and William Batchelor. Quantitative Relationships between Pollen Shed Density and Grain Yield in Maize. Crop Sci. 43:934-942 (2003).
Richard A. Jorgensen, "A Hybrid Seed Production Method Based on the Synthesis of Novel Linkages Between Marker and Male-Sterile Genes", Crop Sci. 43:934-942 (2003).
Communication from the European Patent Office dated May 28, 2016 for Application No. 12 778 014.6.
Hunter, J. L., et al.: "Corn Seed Maturity Indicators and Their Relationship to Uptake of Carbon-14 Assimilate", Crop Science, 1991, vol. 31, pp. 1309-1313.
Ma, B. L., et al.: "Maize kernel moisture, carbon and nitrogen concentrations from silking to physiological maturity", Canadian Journal of Plant Science, 2001, vol. 81, No. 2, pp. 225-232.
Wiersma, D. W., et al.: "Kernel Milkline Stage and Corn Forage Yield, Quality, and Dry Matter Content", Journal of Production Agriculture, Jan. 1993, vol. 6, No. 1, pp. 23-24 and 94-99.
Ciampitti, I.A. et al. "Corn Growth and Development", Jun. 2016.
Communication from the European Patent Office dated Dec. 12, 2016 relating to Rule 71(3) for European patent application No. 12778014.6.
Communication from the European Patent Office dated Apr. 21, 2017 re: decision to grant a patent for European patent application No. 12778014.6 (EP Patent No. 2765845).
Communication from the European Patent Office dated May 18, 2017 re: transmission of the certificate patent for European patent application No. 12778014.6 (EP Patent No. 2765845).
Notice of Opposition by Syngenta to EP Patent No. 2765845 and Syngenta's statement dated Feb. 16, 2018.
Communication from the European Patent Office dated Feb. 28, 2018 re: Notice of Opposition for EP Patent No. 2765845.
Office Action dated Jul. 31, 2018 from Canadian Intellectual Property Office for CA patent application No. 2,852,038.
Office Action dated Jan. 19, 2018 from Eurasian Patent Office for EA patent application No. 201490784. Original and translated version submitted.
Office Action dated Jun. 2, 2017 from Eurasian Patent Office for EA patent application No. 201490784. Original and translated version submitted.
Office Action dated Aug. 5, 2016 from Eurasian Patent Office for EA patent application No. 201490784. Original and translated version submitted.
Wright, H. 1980. Commercial Hybrid Seed Production. In: W. R. Fehr, H. H. Hadley, editors, Hybridization of Crop Plants, ASA, CSSA, Madison, WI. p. 161-176.
Office Action from the Argentine Patent Office dated Nov. 26, 2018 relating to Argentine patent application No. 20120103823 (P12 01 03823). Original and auto-translated version submitted.
Office Action from Eurasian Patent Office dated Feb. 14, 2019 relating to Patent Application No. 201490784. Original and translated version submitted.
Examination Report from the European Patent Office dated Aug. 8, 2018 relating to European Patent Application No. 17165577.2.
Office Action dated Oct. 22, 2019 from Canadian Intellectual Property Office for CA patent application No. 2,852,038.
First Office Action from Chilean Patent Office for CL patent application No. 00949-2014. Original and machine-translated version submitted.
Second Office Action from Chilean Patent Office dated Mar. 13, 2017 for CL patent application No. 00949-2014. Original and machine-translated version submitted.
Denial decision from Chilean Patent Office dated Jun. 11, 2020 for CL patent application No. 00949-2014. Original and machine-translated version submitted.
Communication from the European Patent Office dated Nov. 28, 2019 for European application No. 17165577.2.
European Search Report and Search Opinion dated Jun. 16, 2017 for European application No. 17165577.2.
Minutes of the oral proceedings before the Opposition Division, rejection of the opposition by the Opposition Division, and grounds for decision by the Opposition Division dated Jan. 17, 2020 for European patent No. 2765845 (application No. 12778014.6).
Notice of Appeal dated Mar. 13, 2020 and Written Statement of Grounds of Appeal dated May 14, 2020 for European patent No. 2765845 (application No. 12778014.6).
English translation relating to Ukraine Patent Office Action dated Sep. 8, 2016 for UA patent application No. a201403890.
Rajni et al: "Effect of chemical defoliation on boll opening percentage, yield and quality parameters of Bt Cotton (*Gossypium hirsutum*)", Indian Journal of Agronomy. Mar. 2011, 56(1), pp. 74-77.
Product label for Defol 5 Defoliant/Desiccant with Fire Retardant, Drexel Chemical Company.†
K.H. Knittle & J.S. Burris, "Effect of Kernel Maturation on Subsequent Seedling Vigor in Maize", Crop Sci. 1976; 16:851-855.†
James L. Hunter, "Relationship between the stage of corn seed maturation and assimilate supply, assimilate uptake, and seed quality", Ph.D. Dissertation, University of Kentucky (Jun. 1989).†

\* cited by examiner
† cited by third party

METHODS FOR IMPROVING SEED PRODUCTION IN MAIZE

CROSS-REFERENCE

This utility application claims the benefit of U.S. Provisional Application Ser. No.: 61/547,142 filed Oct. 14, 2011, wherein incorporated herein by reference.

FIELD

The discovery is in the field of plant breeding and improvement, related specifically to a production method which provides advantages, for example, by speeding harvest and increasing the number or proportion of saleable seeds produced.

BACKGROUND

Commercial seed production is a process that involves many steps. In the case of corn (maize), for example, inbred plants must first be crossed in a field under conditions that allow the pollen from the male parent to fertilize the silks on the ear of the female parent in order to produce the hybrid seeds that will be sold to the farmer for further planting. The quality of this hybrid seed impacts its value in the marketplace.

Many factors can affect the quality of hybrid seed. For example, variations in the moisture content, size, shape, or integrity of the harvested crop at the upstream end of the process may influence the effectiveness of each further stage of the hybrid seed production process. Substantial variability in the end product may then result and is undesirable. Further, variations in harvested seed at any stage of production may require recalibration of equipment or other operational adjustments to accommodate the variations. Further still, adjustments to any operating parameter at one step may result in undesirable effects and/or further adjustments at another step. For example, gravity tables may require a relatively consistent flow rate in order to function properly, and hence use of surge bins may be needed in order to equalize flow rates.

Accordingly, there is a need in the art for improved systems and methods of seed production which result in increased quantity or proportion of saleable seed while retaining or improving their germination ability.

The present discoveries relate to these seed production techniques and in particular a technique wherein the plant is treated to induce defoliation at a particular time in development. In certain embodiments, the timing of treatment is based on the moisture content of the developing seed. When a plant is defoliated at the appropriate stage, production of saleable seed is maximized. Seed that is either too large or too small is rejected during post-harvest production operations. Therefore, producing more seed of the commercially desired size and/or shape increases productivity per ear and per field. Defoliating a maize plant at the optimal time based on moisture content of the seed provides improved control of seed size and/or shape, leading to increased productivity in numerous aspects.

Further, seed produced using the disclosed defoliation techniques exhibits improved performance in stressful growing conditions. Seeds from defoliated plants display improved germination and emergence rates, particularly under stress and more uniform stand establishment and higher grain yield relative to seed produced on non-defoliated plants.

Improved plant productivity is advantageous due to the widespread use of maize as human food, livestock feed, and as raw material in industry. The food uses of maize, in addition to human consumption of maize kernels, include both dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries. Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties and ability to suspend particles. The maize starch and flour have application in the paper and textile industries. Other industrial uses include applications in adhesives, building materials, foundry binders, laundry starches, explosives, oil-well muds and other mining applications.

Plant parts other than the grain of maize are also used in industry: for example, stalks and husks are made into paper and wallboard and can be used to make cellulosic ethanol. Cobs are used for bedding, for fuel, and to make charcoal.

SUMMARY

Certain embodiments provide a method of improving production in a maize seed field wherein at least one maize plant is defoliated when the moisture content of the maize plant's developing seed is at or about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70% and the plant is harvested when the moisture content of its developing seed is at or about 10, 11, 12, 13, 14, 15, 16, 17, 18. 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60%.

Certain embodiments provide a means for determining the optimum time for defoliation of an inbred. Factors in the determination include, but are not limited to, environment, genetics and product being utilized.

Use of properly-timed defoliation provides numerous advantages which are discussed throughout this document, including the Figures and the Examples. These advantages include, and are not limited to, greater number of seeds per pound; increased volume or proportion of saleable seed per field and per female acre; decreased discard of seed due to commercially undesirable size or shape; lower moisture content of seed at harvest; earlier harvest date; less fuel and time expended in drying seed for storage; improved performance in laboratory tests for germination at cold temperatures; improved seed treatment efficacy; improved emergence under stress in field conditions; improved plantability in mechanical systems; more uniform stand and improved grain yield.

BRIEF DESCRIPTION OF THE DRAWINGS

The bottom bar chart shows that across 472 seed corn fields in the U.S. Midwest, the DEFOL treatment increased the proportion of saleable seed by approximately 3.4 percentage points. The graph shows the untreated samples had a saleable seed portion of 87.1% whereas the seed harvested from the DEFOL treated area had 90.5% saleable seed. The difference in saleable seed was significant in that P<0.0001.

The upper right bar chart depicts the difference in percent small-seed discard (seed less than 16.5/64" round hole screen) between the two treatments of the seed collected from 472 seed fields across the U.S. Midwest. The percent small seed discard increased from 2.1% in the untreated check ("DEFOL CHECK") to 3.9% ("DEFOL"), for an overall increase of 1.8 percentage points. The difference in small-seed discard percent was significant in that P<0.0001.

The lower left bar chart depicts total size-based discard, i.e. seed too large to sell (large-seed discard) and seed too small to sell (small-seed discard), across the 472 seed fields in the U.S. Midwest. Total size-based discard decreased from 13% in the untreated check area to 9.5% in the DEFOL treated area, for an overall decrease in discard seed of 3.5 percentage points. The difference in total discard seed between the two treatments was significant in that P<0.0001.

DETAILED DESCRIPTION

The embodiments and aspects discussed herein are described in conjunction with systems, tools and methods which are meant to be exemplary and illustrative, and not limiting in scope. In various embodiments, one or more of the above-described problems have been reduced or eliminated, while other embodiments are directed to other improvements.

The disclosure of each reference set forth herein is hereby incorporated by reference in its entirety, to the extent they relate to the materials and methods described herein.

Field crops are bred through techniques that take advantage of the plant's method of pollination. In the practical application of a chosen breeding program, the breeder often initially selects and crosses two or more parental lines, followed by repeated selfing and selection, thereby producing many unique genetic combinations. The breeder can theoretically generate billions of different genetic combinations via crossing, selfing and mutagenesis. Therefore, it is highly unlikely that two breeders will independently develop the same variety having the same traits.

In each cycle of evaluation, the plant breeder selects the germplasm to advance to the next generation. This germplasm is grown under chosen geographical, climatic and soil conditions and optionally subjected to testing for stress tolerance, insect resistance and other traits. Further selections are then made during and after the growing season.

Production techniques are used to manage the propagation of the maize hybrid, seed for which will be sold into the marketplace. A male inbred and female inbred are generally planted in a field with one or more female rows per male row. Plants in the female row are detasseled prior to their producing pollen, thus causing the pollen from the male row to fertilize the ears in the female row. Alternatively, the female may be male sterile and not produce pollen. In any case, the result is that pollen from the male plant fertilizes the ear on the female plant, thus producing hybrid seed. This seed is then harvested.

Harvest techniques can have a significant effect on the quality of the seed. For example, harvest must occur at the right time, when the seed is of the appropriate size and developmental stage. Some techniques, such as those disclosed herein, can be used to increase seed quality at or near the time of harvest and/or during post-harvest storage and handling. These quality attributes may include one or more of the following: greater number of seeds per pound; increased volume or proportion of saleable seed per field and per female acre; decreased discard of seed for commercially undesirable size or shape; lower moisture content of seed at harvest; earlier harvest date; less fuel and time expended in drying seed for storage, which also reduces investment in dryer capacity; improved seed integrity during post-harvest treatments due to reduced embryo exposure in flatter seeds; improved performance in laboratory tests for germination at cold temperatures or under other stressful conditions; more uniform coverage of seeds by chemical seed treatments, thereby improving efficacy of the treatment; reduced weight of the industry-standard 80,000-kernel bag of seed, providing ergonomic advantages for an aging farmer population; improved plantability in mechanical systems; improved emergence under stress in field conditions; more uniform stand establishment and improved grain yield.

In one embodiment, the instant disclosure provides optimized treatment of the female inbred carrying the ear comprising the hybrid seed, in order to produce a greater number or greater proportion of saleable seed. Saleable seed is that which, among other traits, is viable and is of commercially desirable size and shape.

The defoliation treatment comprises hastening the browning of leaf material and stopping or significantly reducing the manufacture of photosynthates and/or the movement of photosynthates from the leaf to the ear. This can be accomplished through, for example, spraying the production field with any of a number of salt or herbicide defoliant solutions, including but not limited to IGNITE®, diquat, paraquat, glyphosate and sodium chlorate. Alternatively or additionally, defoliation may occur by mechanical means, by manual means, or by any combination of manual, mechanical and/or chemical means. In certain embodiments more than one defoliation treatment may occur. The claimed process is not dependent on the method in which the plant is defoliated. Methods are applicable to male-sterile as well as male-fertile plants. A control plant or control field or control treatment will correspond to the test plant or field except that it does not receive the defoliation treatment.

Previous defoliation methods were designed to improve seed vigor without reducing seed size. See, for example, U.S. Pat. No. 6,162,974, at Column 4: "The size of seeds in a maize seed harvest is an important commercial consideration because larger seed size is preferred in the marketplace." In contrast, current defoliation methods are designed to impact seed size and shape, deliberately producing smaller, flatter, more uniform seed.

Also, previous defoliation methods relied on Growing Degree Days (GDD) or Growing Degree Units (GDU) to determine an appropriate time for defoliation. Impact of GDD on plant maturation varies across inbreds (as shown in Table 1 of U.S. Pat. No. 6,162,974). In addition, GDD must be recalculated each day of each year and the interaction between GDD and plant maturation is complicated by such factors including but not limited to soil type and precipitation. Thus a defoliation method based on GDD is subject to environmental variability.

In contrast, seed moisture level is a stable characteristic, consistent for an inbred across locations and across years even with varying weather conditions and therefore is more reliably predictive of the optimum time for defoliation. Determination of the optimum seed moisture level at which to cause defoliation is accomplished through extensive testing and calibration of the effects of defoliation, encompassing variables of genetics, treatment type, timing of treatment and environmental conditions.

Use of properly-timed defoliation based upon seed moisture content provides numerous advantages which include, and are not limited to, greater number of seeds per pound; increased volume or proportion of saleable seed per field and per female acre; decreased discard of seed due to commercially undesirable size or shape; lower moisture content of seed at harvest; earlier harvest date; less fuel and time expended in drying seed for storage; improved performance in laboratory tests for germination at cold temperatures; improved seed treatment efficacy; improved emergence under stress in field conditions; improved plantability in mechanical systems; more uniform stand; fewer runt plants and improved grain yield.

The key factors in that determination (inbred choice) are the starting seed size (kernels per pound) and the stress emergence ability of the female (germination). The seed size is a more critical component since defoliation can make seeds too small leading to unacceptable levels of discard.

The other component is choosing inbreds that are likely to respond to defoliation by producing hybrids with higher germination and crop establishment, especially under stressful conditions. Choosing these inbreds involves characterizing the stress emergence trait for hybrids with these inbreds as females. This is accomplished by evaluating the material in a combination of laboratory germination tests and early-planted field tests. The combined data is used to assign a stress emergence score which characterizes the ability of the material to emerge under stressful conditions. Inbreds that are predicted to produce hybrids with below average stress emergence scores are considered as defoliation candidates.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells, reference to "a seed" includes plurality of such seeds and equivalents thereof known to those skilled in the art, and so forth.

"Determining" or "determination" refers to measuring, assessing, evaluating, estimating, monitoring and/or predicting. "Defoliant" is any compound that will slow or stop the production of photosynthates, and/or movement of photosynthates from the leaf to the ear, and includes but is not limited to herbicides and salt compositions that may kill the plant. These compositions can also include surfactants.

"Defoliation" means removal, destruction, or desiccation of a substantial proportion of leaf tissue of a plant, generally at least 50%, up to and including 100%. Defoliation can occur by chemical or physical (mechanical and/or manual) means, or by any combination of such means. A combination of physical and chemical means of defoliation may be particularly advantageous in conditions such as drought which may otherwise result in poor pollination and development of a small number of large kernels.

The term "emerge" or "emergence" refers to the appearance of a seedling shoot above the germination medium, for example the soil surface in a field.

The term "emergence rate" refers to a percentage of planted seeds that emerge. For example, 80% emergence rate indicates 80 of 100 planted seeds emerge.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "germination" refers to the initial stages in the growth of a seed to form a seedling. A seed is considered germinated if it shows signs of radicle (root) or shoot protrusion or if the emerging seedling structures meet specific criteria such as those of the International Rules for Seed Testing (International Seed Testing Association, ISTA) or the Association of Official Seed Analysts, Inc., AOSA).

The term "germinated" may refer to a seed that has produced a viable plant seedling with or without exposure to light in a germination chamber, growth cabinet, greenhouse or the field.

The term "germination rate" or "germination percentage" refers to a percentage of planted seeds that emerge. For example, 80% emergence rate indicates 80 of 100 planted seeds emerge.

A "hybrid plant" or "hybrid progeny" is an individual produced from genetically different parents (i.e., a genetically heterozygous or mostly heterozygous individual). Typically, the parents of a hybrid differ in several important respects. Hybrids are often more vigorous than either parent, but they cannot breed true.

The term "hybrid variety" refers to a substantially heterozygous hybrid line and minor genetic modifications thereof that retain the overall genetics of the hybrid line including but not limited to a locus conversion, a mutation or a somoclonal variant.

"Increased germination under stressed conditions" as used herein is a measure of the seed's ability to germinate under stressed conditions, including but not limited to conditions such as cold, saturated soils, drought, flooding and heat, as compared to a seed of matching genetics germinating under the same stressed conditions.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells and/or progeny of the same. A plant cell is a cell of a plant, taken from a plant or derived through culture from a cell taken from a plant. Plant cells include, without limitation, cells from seeds, suspension cultures, embryos, meristematic regions, callus tissue, leaves, roots, shoots, gametophytes, sporophytes, pollen and microspores.

The term "progeny" refers to the descendants of a particular plant (self cross) or pair of plants (cross-pollinated). The descendants can be, for example, of the $F_1$, the $F_2$, or any subsequent generation.

The term "runt(s)" refers to a plant or seedling that is visually smaller than the neighboring plants in the field. A plant is considered a runt if it is one or two leaf stages behind the average for the surrounding plants, or if its height is reduced by one third or more compared to surrounding plants. The terms "runt(s)" and "uniformity" are often used to describe similar phenotypes whereby fewer runts are associated with increased uniformity of seed emergence or stand establishment and vice versa.

"Seed" as used herein refers to a hybrid or inbred plant part comprising an embryo.

"Stand establishment" as used herein is the ability of a group of seeds to emerge and form normal seedlings, commonly under field conditions. Stand establishment may also be referred to as plant stand or crop establishment.

"Stress", "stressed conditions" and related terms refer to any factors that decrease plant growth and reproduction below the plant's genotypic potential including, but are not limited to, cold soil, flooding (submergence), cold rain, frost, snow, soil compaction, and excessive residue from previous crops. Stress tolerance refers to the ability of a plant or crop species to withstand stress.

"Seed moisture" can be determined in a number of ways, but often an Ohaus© Moisture Balance is employed and used as per manufacturer instructions. Seed moisture is an important measure as it indicates maturation of the seed and affects susceptibility to some diseases. Other methods of determining seed moisture include, but are not limited to, incubator-drying, drying cabinets, forced air drying, oven drying, microwave drying, sun drying and drying over saturated salt solutions (see, Abendroth, et al., (2011) PMR 1009, Corn Growth and Development, Iowa State University and Winston and Bates, (1960) *Ecology* 41:232-237.) Various desiccants may be used in combination with seed drying methods. Seeds may be dried at a range of temperatures, including room temperature and ambient outdoor temperature, with or without air circulation.

The present invention further relates to transgenic plant cells and transgenic plants transformed to contain and express a polynucleotide. "Transformed", "transfected" or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector. Various methods of plant transformation are currently known and available. For example, the introduction of DNA sequences into plants and/or plant cells can be accomplished by Agrobacterium-mediated transformation, viral vector mediated transformation, electroporation and microprojectile bombardment mediated transformation (particle gun or biolistics methods). The DNA sequence may also be transformed directly into the plastid genome by plastid transformation. As used herein, the term "plastid" means the class of plant cell organelles that includes amyloplasts, chloroplasts, chromoplasts, elaioplasts, eoplasts, etioplasts, leucoplasts and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region.

Transgenic events can include traits for herbicide resistance, drought, yield, oil content of the seed and starch content of the seed, carbon partitioning within the seed, insecticide resistance or any one or more myriad other traits.

Seed treatments and coatings may be used on seeds produced using the disclosed methods. Use of seed coatings and treatments is known in the art; see, for example, U.S. Pat. No. 5,876,739. The combination of the defoliation treatment and the seed treatment/coating may provide desirable additive effects. Although it is believed that seed treatments can be applied to a seed in any physiological state, it is preferred that the seed be in a sufficiently durable state that no damage is incurred during the treatment process. Typically, the seed would be a seed that had been harvested from the field, removed from the plant and separated from any other non-seed plant material. The seed would preferably also be biologically stable to the extent that the treatment would cause no biological damage to the seed. Better coverage with the seed treatment formulation occurs with the smaller, flatter seed produced by the methods disclosed herein; in turn, better coverage can provide improved efficacy. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment. Within the limitations just described, it is believed that the treatment can be applied to the seed at any time between harvest of the seed and sowing of the seed.

As used herein, the term "unsown seed" is meant to include seed at any period between the harvest of the seed and the sowing of the seed in the ground for the purpose of germination and growth of a plant.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Agronomically and commercially important products and/or compositions of matter, including but not limited to animal feed, commodities and seed products and by-products that are intended for use as food for human consumption or for use in compositions that are intended for human consumption, including but not limited to flour, meal, syrup, oil, starch, foods containing seeds or seed parts and seed by-products, and the like are contemplated if these products and compositions of matter are derived from or obtained directly from a seed produced using methods of the present invention. Such products and/or compositions are also referred to herein as biological samples. The biological samples can be derived from the plant, the plant tissue, or the seed produced by the plant.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

The examples described herein are meant to be representative and as examples of the discoveries, and are not limiting to the scope of the claims.

Example 1

Implementation of Defoliation Treatment

In 2010, within 472 seed fields across the Midwest United States, entire fields were treated with Defol® 750 (sodium chlorate from Drexel Chemical Company) according to manufacturer's direction and an untreated check strip area was left in each field (i.e., untreated test strip was not sprayed with defoliating agent). The check strip area was the width of a spray boom and the length of the seed field within a representative area of the seed field. Defol® 750 was applied at 55-60% seed moisture which was determined using an Ohaus® MB35 moisture balance. After treatment, seed was allowed to dry naturally in the field until approximately at or near physiological maturity (~32% seed moisture). One to two days prior to machine harvest of the field, all harvestable ears from 12 consecutive plants in 3 different areas of each treatment (DEFOL, untreated check) were husked and placed in burlap bags. A tag indicating location, field number, and treatment was placed on the outside and inside of the bag. A harvestable ear was described as an ear equal to or greater than 4 inches in length with more than 30 kernels. Ears with more than 25% damage from disease or insects were not included. Burlap bags were transported to the local production facility and dried in the lower tunnels of the large production dryers for 3 to 4 days (or until approximately 12% seed moisture). Seed moisture at the time of harvest was determined from the samples collected from each treatment area using a DICKEY-John® GAC® moisture tester.

A small plot sheller (AEC small batch sheller) was used to shell seed from the cob. Once shelled, the seed was passed over a sample sizer equipped with screens of $23/64$ inch round holes (RH) and 16.5/64 inch RH. Seed that remained on top of the $23/64$" RH screen is considered too large to sell (large-seed discard). Seed that passes through the 16.5/64 RH screen is considered too small to sell and is discarded (small-seed discard). Seed that passes through the $23/64$" RH screen but remains on top of the 16.5/64 " RH screen is considered saleable seed in terms of size and shape. From the saleable seed, the number of kernels in 0.25 pounds of the saleable seed was counted using a bowl seed counter to determine kernels per pound. Statistical analysis was performed using T-test procedures of the Statistical Analysis System (SAS Inst., Cary N.C.). Uniform seed, and particularly flatter, smaller, uniform seed, are preferred for ease and efficiency of treating, packaging, shipping, handling and planting. In addition, seeds that are less round have reduced incidence of "raised-embryo" syndrome. Raised embryos increase susceptibility to physical damage during seed conditioning and handling.

In addition, defoliation treatment hastens maturation and dry-down so that harvest can typically occur 4 to 5 days earlier than the untreated check under typical harvest conditions and up to 14 days earlier under cooler weather conditions. This is advantageous in preventing field losses due to inclement weather. It also reduces fuel and dryer capacity required for post-harvest drying.

Example 2

Defoliation Treatment Produces Seed with Improved Stand Establishment and Final Grain Yield Hybrid seeds produced from fields treated with Defol® 750 and from untreated check strips were planted in seven field locations in spring 2011. Seeds from defoliated and check hybrids were produced in the same seed fields in 2010. Seeds were planted between April 12 and May 18 in Eau Claire, Wis., Janesville, Wis., Schuyler, Nebr., Minburn, Iowa, Flandreau, S. Dak., Johnstown, N. Dak. and Coteau du Lac, Canada. Crop emergence was evaluated at the V3 to V4 stage in all locations and emergence was recorded as the percent of planted seeds that emergence and produced normal seedlings. For example, if 30 seeds were planted and 21 seeds emerged, emergence is reported at 70%.

Figure 1:
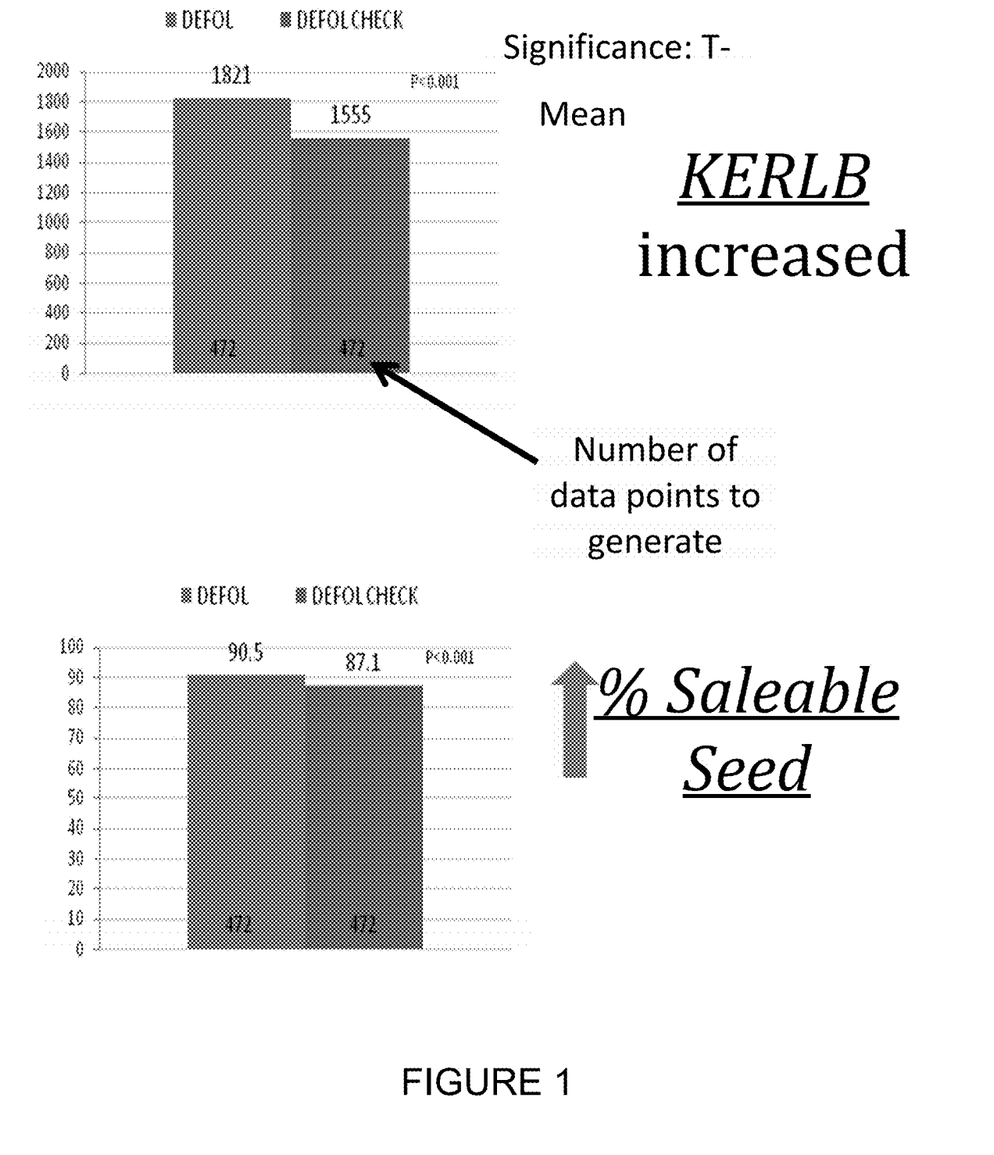
FIG. 1—The top bar chart shows that across 472 seed corn fields of various hybrids, the defoliation treatment ("DEFOL" or "DEFOL application" or "DEFOL treatment") resulted in an average of 1821 seeds per pound, which is an increase of 266 kernels, or 17%, over the untreated check ("DEFOL CHECK"), which yielded an average of 1555 seeds per pound. The difference in kernels per pound between DEFOL and untreated was significant (P<0.001).
Figure 2:
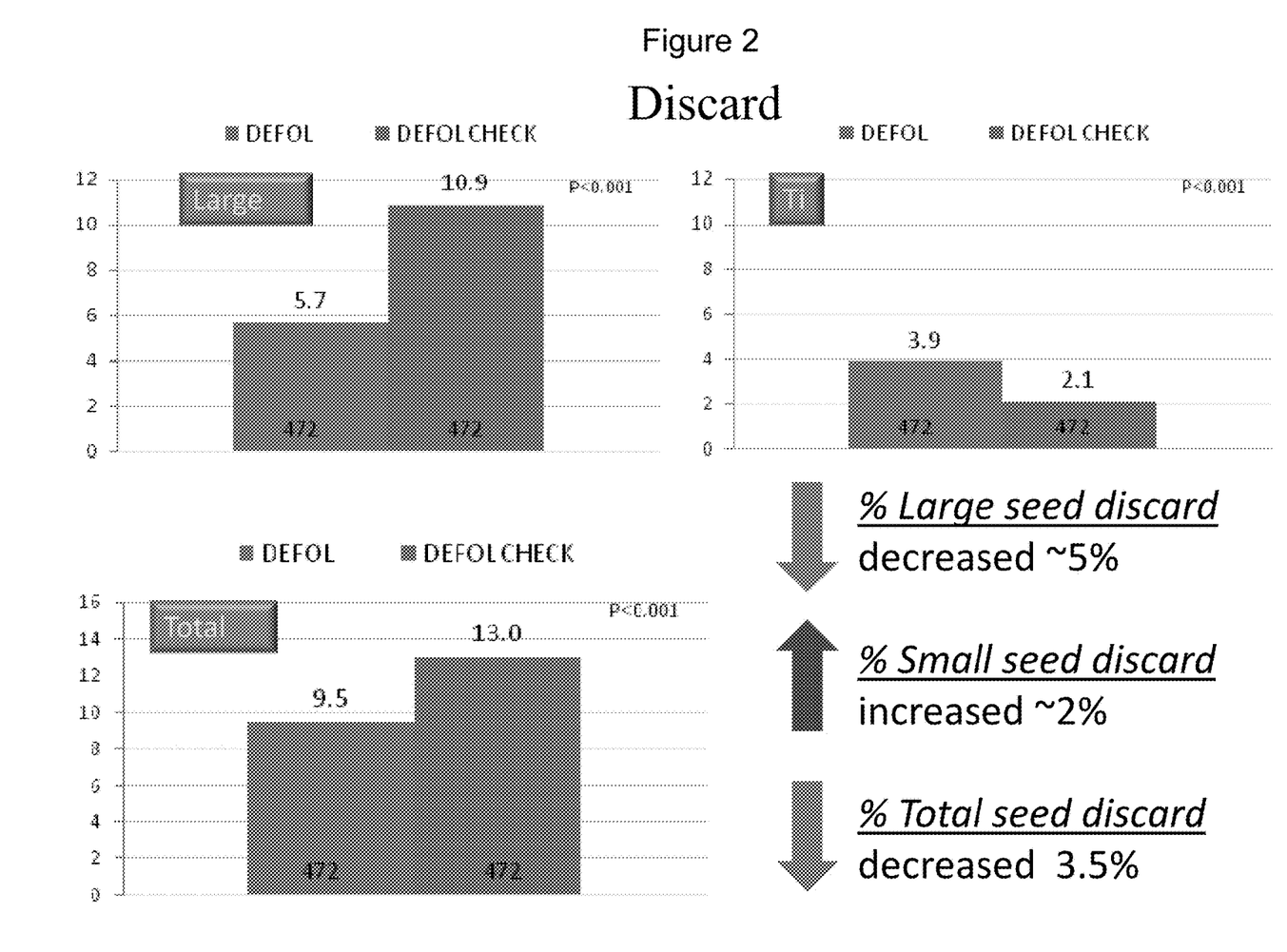
FIG. 2—The upper left bar chart depicts the difference in percent large-seed discard (seed greater than 23/64" round hole screen) between two treatments from 472 seed fields across the U.S. Midwest. The percent large-seed discard decreased from 10.9% to 5.7% with the use of DEFOL, for an overall decrease of large seed discard of 5.2 percentage points. The difference in large seed discard between the two treatments was significant in that P<0.0001.
Figure 3:
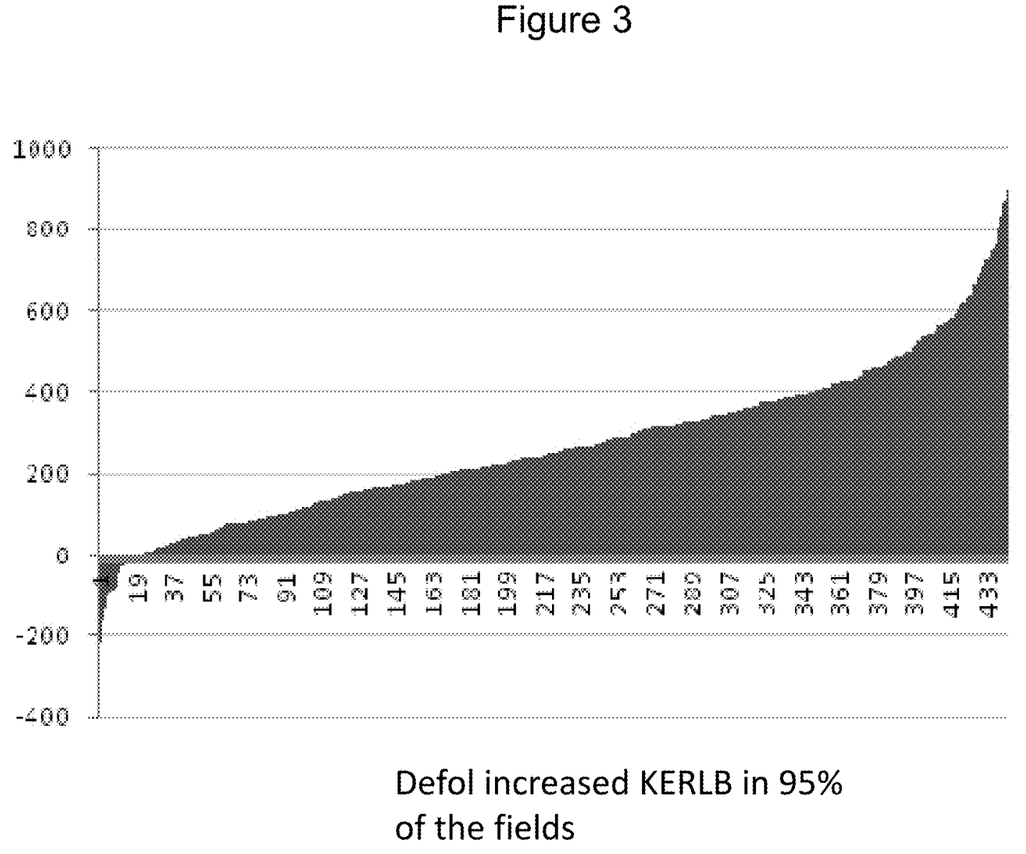
FIG. 3—This graph depicts the difference in kernels per pound for seed from the DEFOL treated area and seed from the untreated area across 472 seed fields in the U.S. Midwest. In 95% of the 472 seed fields, the number of kernels per pound ("KERLB") was greater in the DEFOL treated area than in the untreated area.
Figure 4:
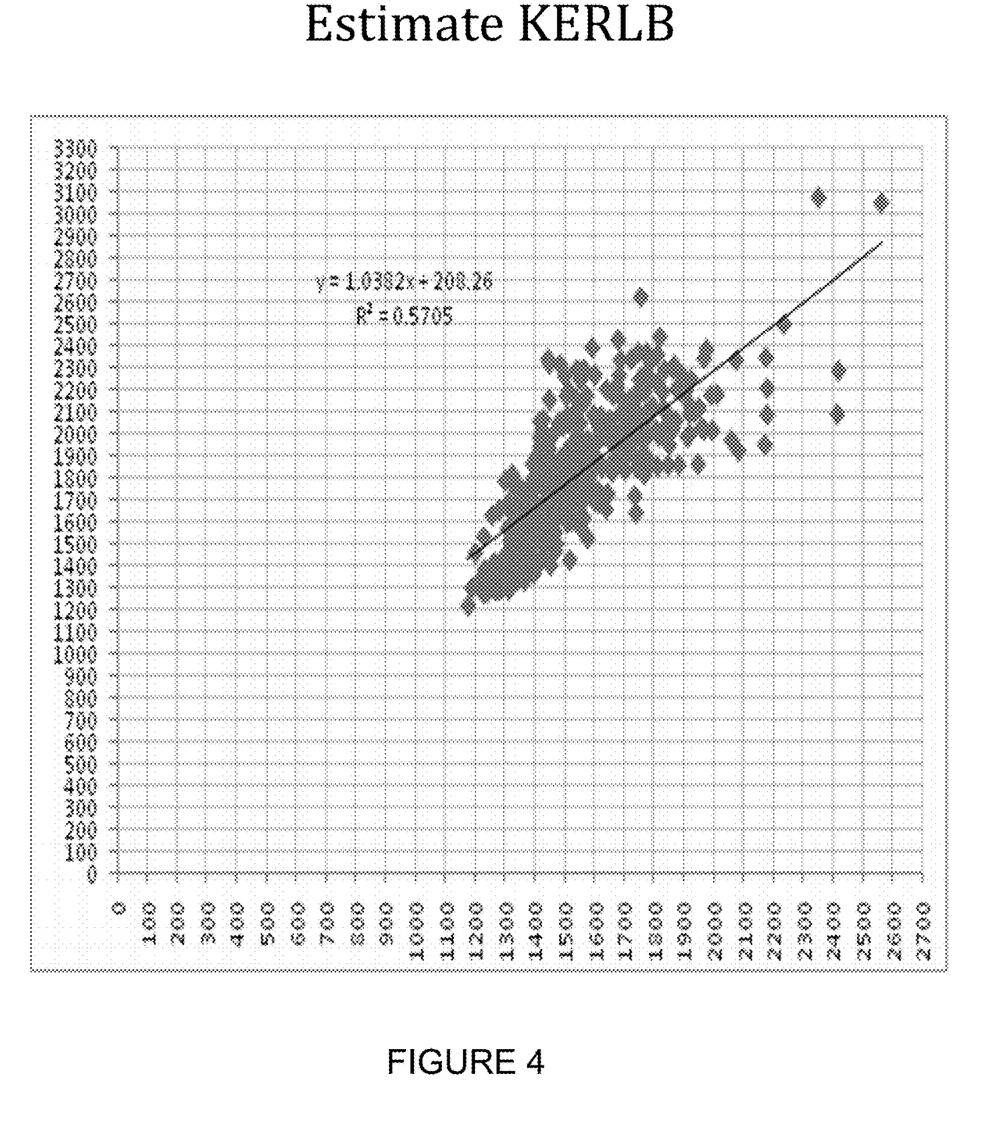
FIG. 4—This graph represents the correlation, and provides a prediction, between the kernels per pound of seed in the untreated area and kernels per pound of seed in the treated area. The regression equation provides an estimate of the kernels per pound following a DEFOL treatment made at about 60% developing-seed moisture, based on kernels per pound of the untreated inbred. For example, if an inbred typically produces seed of 1500 kernels per pound, a DEFOL application at around 60% grain moisture would increase the number of kernels per pound to 1766 ((1.0382×1500)+208.26).
Figure 5:
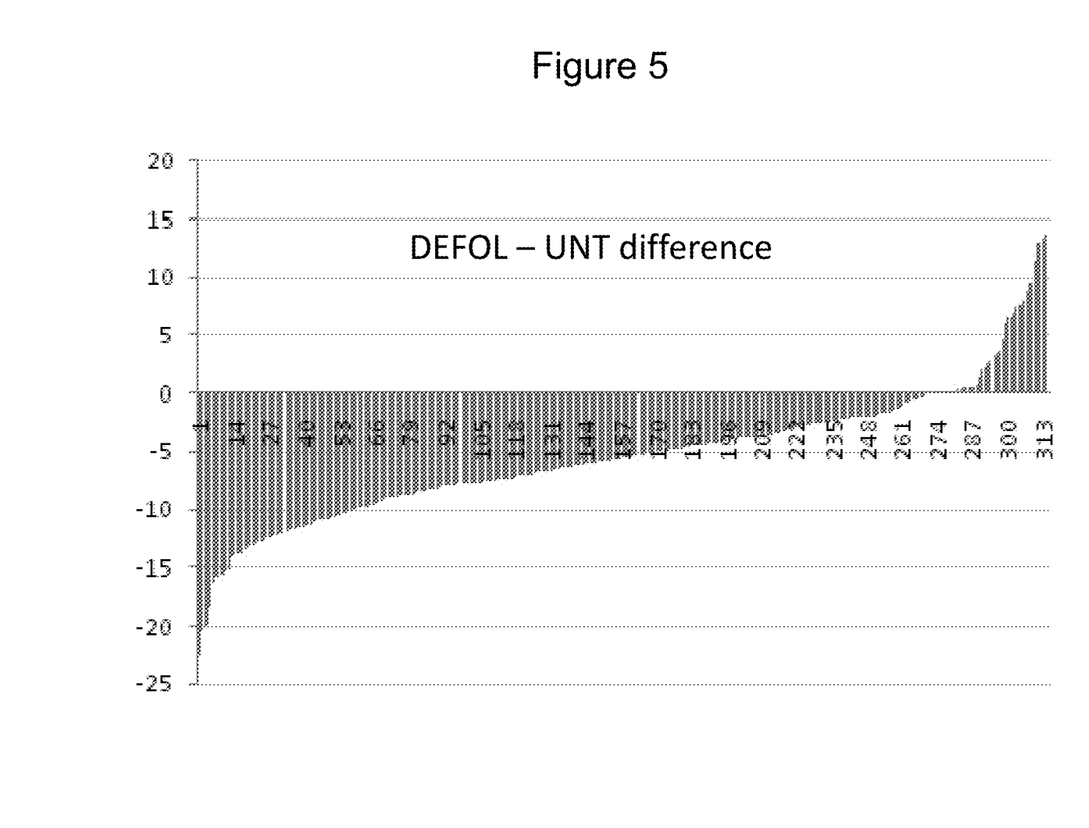
FIG. 5—This graph depicts the difference in harvest grain moisture in the seed from the treated area ("DEFOL") and that of the untreated ("UNT") area from 313 seed fields in the U.S. Midwest. Bars below the 0 x-axis line indicate that the seed in the DEFOL treated area was of lower grain moisture than the seed in its corresponding untreated area. The y-axis indicates the percentage moisture points difference in harvest grain moisture in the seed from the treated area ("DEFOL") and that of the untreated ("UNT") area from 313 seed fields in the U.S. Midwest.
Figure 6:
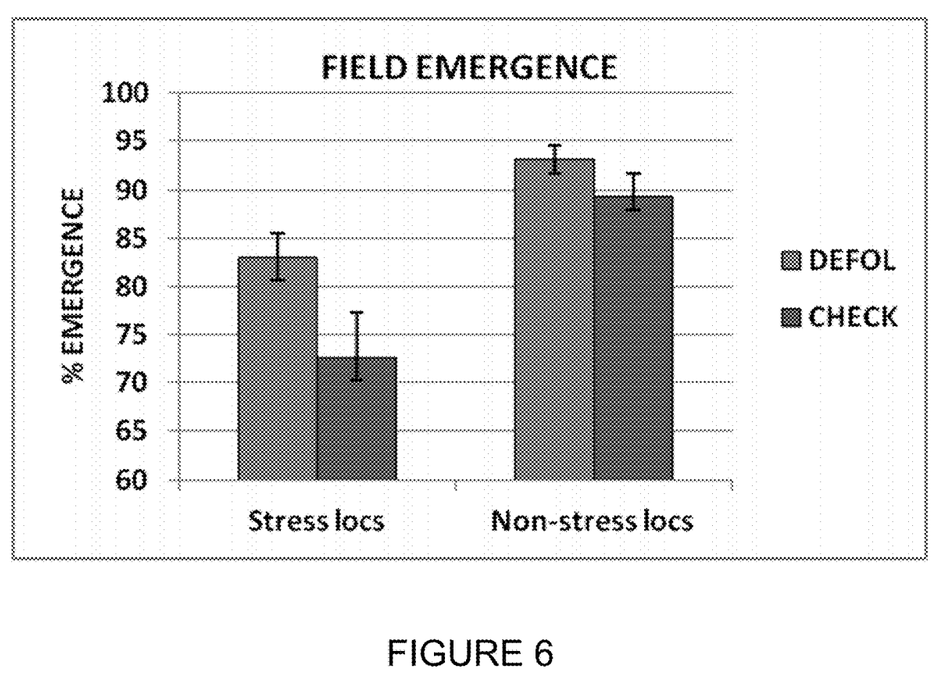
FIG. 6—This chart depicts the % field emergence (crop establishment) for treated ("DEFOL") and untreated ("CHECK") seeds in stress and non-stress field locations. Each of the bars represents the average % emergence for 16 Pioneer hybrids. Treated and untreated seeds from each hybrid were produced in the same seed fields in 2010 (see, Example 1). Seeds were planted in the field in spring 2011. Locations were considered stressful ("Stress locs") if the average emergence of all hybrids was 85% or less or if the soil temperature remained at 10° C. or below for two weeks after planting. Locations where average % emergence of all hybrids was greater than 85% were considered "Non-stress locs". The following locations were considered "Stress locs": Eau Claire, Wis.; Janesville, Wis.; Schuyler, Nebr.; Minburn, Iowa; Flandreau, S. Dak. "Non-stress" locs were Johnstown, N. Dak. and Coteau du Lac, Canada.
Figure 7:
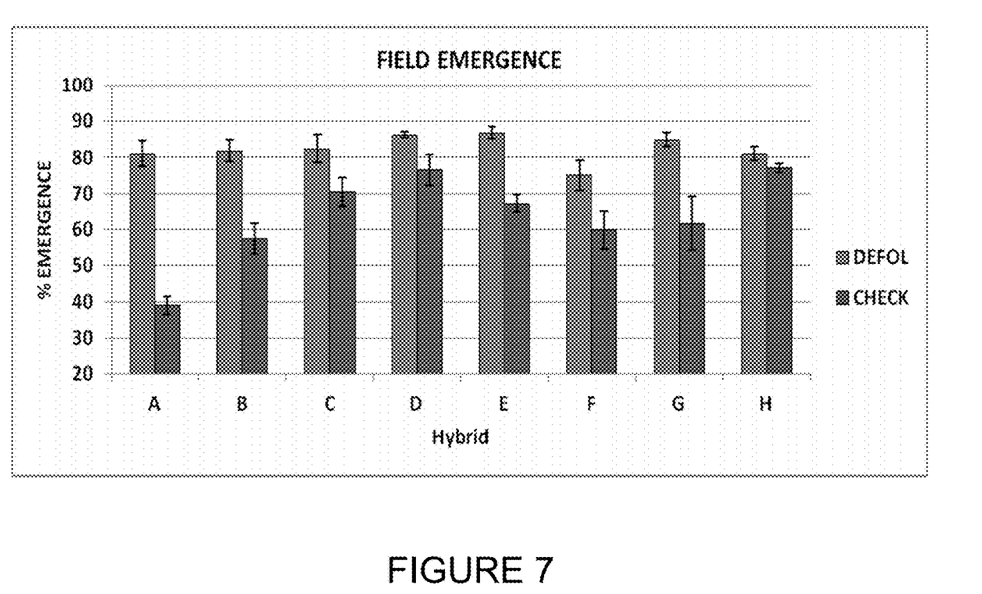
FIG. 7—This bar chart depicts the % field emergence (crop establishment) for treated ("DEFOL") and untreated ("CHECK") seeds from eight Pioneer hybrids. Treated and untreated seeds from each hybrid were produced in the same seed fields in 2010 (see, Example 1). Seeds were planted in spring 2011 at the following locations: Eau Claire, Wis.; Janesville, Wis.; Schuyler, Nebr.; Minburn, Iowa; Flandreau, S. Dak. The bars represent the average % emergence across all locations.
Figure 8:
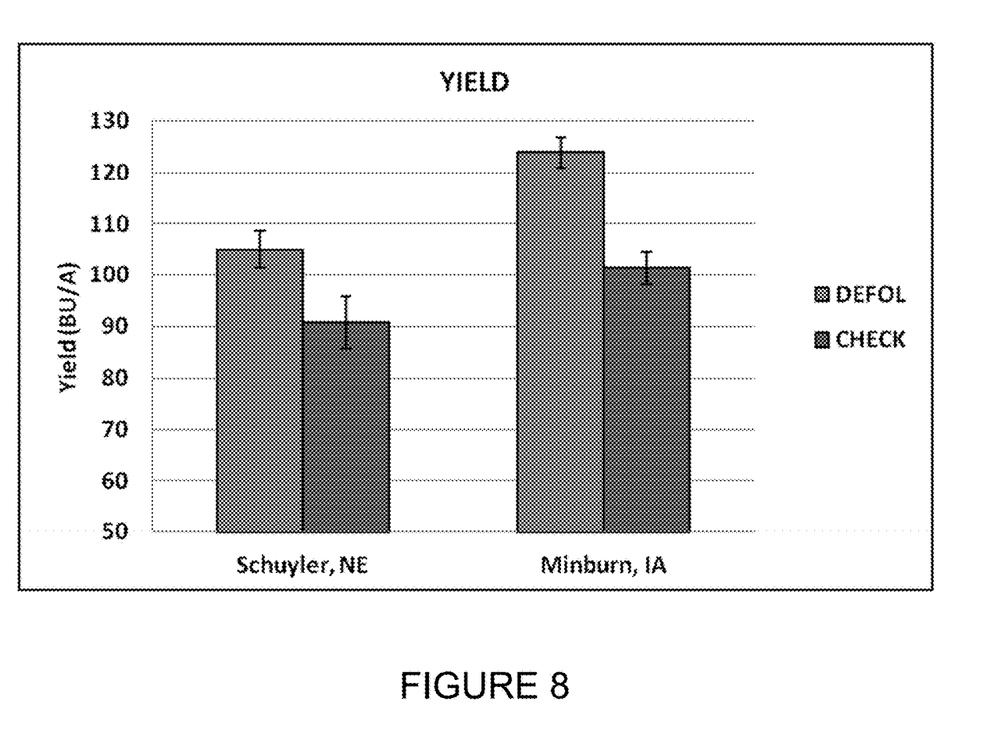
FIG. 8—This bar chart depicts the yield in bushels per acre for treated ("DEFOL") and untreated ("CHECK") seeds in two field locations. Each of the bars represents the average yield for 15 Pioneer hybrids. Treated and untreated seeds from each hybrid were produced in the same seed fields in 2010 (see, Example 1). Seeds were planted in spring 2011.

A location was considered stressful if the average emergence of all hybrids was 85% or less or if the soil temperature remained at 10° C. or below for two weeks after planting. Locations where average % emergence of all hybrids was greater than 85% were considered non-stressful. The following locations were considered stressful: Eau Claire, Wis.; Janesville, Wis.; Schuyler, Nebr.; Minburn, Iowa; Flandreau, S. Dak. Collectively these locations had average emergence of 74%. Non-stressful locations were Johnstown, N. Dak. and Coteau du Lac, Canada, which together averaged 91% emergence. On average, seeds from defoliated hybrids had 10% higher emergence in stressful locations and 4% higher emergence in non-stressful locations, compared to non-defoliated checks (FIG. 6). FIG. 7 shows the difference in % emergence for eight individual defoliate and check hybrids in the test.

Yield data was collected at the Schuyler, Nebr. and Minburn, Iowa. Fifteen hybrids produced from defoliation and check treatments were harvested by hand at approximately 18% moisture and the data was pooled across the two locations, on average, seeds from defoliated hybrids had approximately 14 additional bushels per acre at the Schuyler location and approximately 23 additional bushels per acre at the Minburn location.

What is claimed is:

1. A method of increasing production of saleable maize seed from a hybrid seed production field, the method comprising:
   a. determining the percentage of moisture content of a maize hybrid seed from a fertilized maize female inbred plant in the hybrid seed production field, wherein the field comprises maize female inbred plants that have been fertilized by pollen from maize male inbred plants; and
   b. treating the fertilized maize female inbred plants in the hybrid seed production field with a chemical means for defoliation, when the % seed moisture is between 45%-70%, wherein the fertilized maize female inbred plants are defoliated by said treatment, thereby increasing production of saleable maize seed from the hybrid seed production field.

2. The method of claim 1, wherein multiple defoliation treatments are made.

3. The method of claim 1, wherein the saleable maize seed has an increased proportion of flat seed compared to control seed produced from a field not treated with the chemical means for defoliation.

4. The method of claim 1, wherein the number of kernels per pound in the saleable seed is increased compared to the number of kernels per pound produced from a field not treated with the chemical means for defoliation.

5. The method of claim 1, further comprising:
   harvesting the saleable maize seed, wherein the harvested saleable maize seed exhibits, relative to a control seed produced from a field not treated with the chemical means for defoliation, one or more of: reduced moisture at harvest; reduced post-harvest dry-down requirement; greater size consistency; improved germination percentage or emergence rate under laboratory stress test; improved mechanical plantability; increased emergence percentage or emergence rate in field conditions; more uniform emergence in field conditions; fewer runt or stunted seedlings; and increased grain yield.

6. The method of claim 1, further comprising:
   (a) harvesting the saleable maize seed, wherein the saleable maize seed is harvested at between about 20% and 45% moisture.

7. The method of claim 1, wherein the female or male plants or both comprise a transgenic event conferring a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

8. A method of developing seed which has increased germination percentage, emergence rate and increased uniformity of emergence under field conditions, the method comprising:
   a. determining the percentage of moisture content of a maize hybrid seed from a fertilized maize female inbred plant in a hybrid seed production field, wherein the field comprises maize female inbred plants that have been fertilized by pollen from maize male inbred plants;
   b. treating the fertilized maize female inbred plants in the hybrid seed production field with a chemical means for defoliation, when the % seed moisture of a seed from the hybrid seed production field is between 45%-70% wherein the fertilized maize female inbred plants in the field are defoliated by said treatment.

9. The method of claim 8, wherein multiple defoliation treatments are made.

10. The method of claim 8, wherein the saleable maize seed has an increased proportion of flat seed compared to control seed produced from a field not treated with the chemical means for defoliation.

11. The method of claim 8, wherein the number of kernels per pound in the saleable seed is increased compared to the number of kernels per pound produced from a field not treated with a chemical means for defoliation.

12. The method of claim 8, further comprising:
   harvesting the saleable maize seed, wherein the harvested saleable maize seed exhibits, relative to a control seed produced from a field not treated with the chemical means for defoliation, one or more of: reduced moisture at harvest; reduced post-harvest dry-down requirement; greater size consistency; improved germination percentage or emergence rate in laboratory stress tests; improved mechanical plantability; increased emergence percentage or emergence rate in field conditions;

more uniform emergence in field conditions; fewer runt or stunted seedlings; and increased grain yield.

13. The method of claim 8, further comprising:
harvesting the saleable maize seed, wherein the saleable maize seed is harvested at between about 20% and 45% moisture.

14. The method of claim 8, wherein the female or male plants or both comprise a transgenic event conferring a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

15. A method of reducing the amount of discarded seed from a maize hybrid seed production field, the method comprising:
a. determining the percentage of moisture content of a maize hybrid seed from a fertilized maize female inbred plant in the hybrid seed production field, wherein the field comprises maize female inbred plants that have been fertilized by pollen from maize male inbred plants;
b. treating the fertilized maize female inbred plants in said maize hybrid seed production field with a chemical means for defoliation, when the moisture content of a seed from the maize hybrid seed production field is between 45%-70%, and wherein the fertilized maize female inbred plants in the field are defoliated by said treatment;
b. harvesting the seed; and
c. discarding seed that is a commercially undesirable size or shape, thereby decreasing discarded seed.

16. The method of claim 15, wherein discard for large seed and/or small seed is decreased compared to control seed produced from a field not treated with the chemical means for defoliation.

17. A method of increasing production of saleable maize seed from a hybrid seed production field, comprising:
a. determining the moisture content of a maize hybrid seed from a fertilized maize female inbred plant in the hybrid seed production field, wherein the field comprises maize female inbred plants that have been fertilized by pollen from maize male inbred plants; and
b. treating the fertilized maize female inbred plants in the production field with a chemical defoliant, when the percentage moisture content of the seed is between 45%-70%, wherein the fertilized maize female inbred plants in the field are defoliated by said treatment, thereby increasing production of saleable maize seed from the hybrid seed production field.

18. The method of claim 17, wherein multiple treatments with the defoliant are made.

19. The method of claim 17, wherein the saleable maize seed has an increased proportion of flat seed compared to control seed produced from a field not treated with the defoliant.

20. The method of claim 17, wherein the number of kernels per pound in the saleable seed is increased compared to the number of kernels per pound produced from a field not treated with the defoliant.

21. The method of claim 17, further comprising, harvesting the saleable maize seed, wherein the harvested saleable maize seed exhibits, relative to a control seed produced from a field not treated with the chemical defoliant, one or more of: reduced moisture at harvest; reduced post-harvest drydown requirement; greater size consistency; improved germination percentage or emergence rate under laboratory stress test; improved mechanical plantability; increased emergence percentage or emergence rate in field conditions; more uniform emergence in field conditions; fewer runt or stunted seedlings; and increased grain yield.

22. The method of claim 17, further comprising:
harvesting the saleable maize seed, wherein the saleable maize seed is harvested at between about 20% and 45% moisture.

23. The method of claim 17, wherein the female or male plants or both comprises a transgenic event conferring a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

24. The method of claim 1, further comprising determining the percentage of moisture content of the maize hybrid seed in step a using a moisture balance.

25. The method of claim 8, further comprising determining the percentage of moisture content of the maize hybrid seed in step a using a moisture balance.

26. The method of claim 17, further comprising determining the percentage of moisture content of the maize hybrid seed in step a using a moisture balance.

27. The method of claim 5, further comprising harvesting the saleable maize seed at a date earlier than a control seed produced from a field not treated with the chemical means for defoliation.

28. The method of claim 12, further comprising harvesting the saleable maize seed at a date earlier than a control seed produced from a field not treated with the chemical means for defoliation.

29. The method of claim 21, further comprising harvesting the saleable maize seed at a date earlier than a control seed produced from a field not treated with the chemical defoliant.

* * * * *